(12) United States Patent
Pattekar et al.

(10) Patent No.: US 10,319,000 B2
(45) Date of Patent: Jun. 11, 2019

(54) COMPUTER-IMPLEMENTED SYSTEM AND METHOD FOR REAL-TIME FEEDBACK COLLECTION AND ANALYSIS

(71) Applicant: Palo Alto Research Center Incorporated, Palo Alto, CA (US)

(72) Inventors: Ashish V. Pattekar, Cupertino, CA (US); Ramkumar Abhishek, Mountain View, CA (US); Alan G. Bell, Los Altos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 411 days.

(21) Appl. No.: 14/262,632

(22) Filed: Apr. 25, 2014

(65) Prior Publication Data
US 2015/0310508 A1 Oct. 29, 2015

(51) Int. Cl.
*G06Q 50/00* (2012.01)
*G06Q 30/02* (2012.01)
(Continued)

(52) U.S. Cl.
CPC ......... *G06Q 30/0282* (2013.01); *G06Q 50/22* (2013.01)

(58) Field of Classification Search
CPC ........ G06Q 50/22; G06Q 50/24; G06Q 40/08; G06Q 10/10; G06F 19/322; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50;
(Continued)

(56) References Cited

U.S. PATENT DOCUMENTS

2002/0111826 A1* 8/2002 Potter .................. G06F 19/327
705/2
2002/0133379 A1* 9/2002 Lewis .................. G06Q 10/06
705/4
(Continued)

*Primary Examiner* — Tran N Nguyen
(74) *Attorney, Agent, or Firm* — Krista A. Wittman

(57) ABSTRACT

A computer-implemented system and method for real-time feedback collection and analysis is provided. An event related to a patient is identified during the patient's visit to a medical care facility. A prompt soliciting feedback is triggered upon identification of the event and the prompt is provided to the patient with at least one inquiry regarding the event. Feedback regarding the event is provided by the patient during the patient's visit to the medical care facility in response to the prompt. The feedback is analyzed and a recommendation for intervention of the patient's care is provided during the patient's visit to the medical care facility based on the feedback analysis.

20 Claims, 6 Drawing Sheets

(51) Int. Cl.
  *G06Q 50/22* (2018.01)
  *G06Q 10/00* (2012.01)
(58) Field of Classification Search
  CPC ........ G16H 50/70; G16H 50/80; G16H 70/00;
  G16H 70/20; G16H 70/14; G16H 70/60;
  G16H 80/00
  See application file for complete search history.

(56) References Cited

U.S. PATENT DOCUMENTS

| | | | |
|---|---|---|---|
| 2003/0016122 A1* | 1/2003 | Petrick | A61B 5/117 340/10.41 |
| 2008/0059230 A1* | 3/2008 | Manning | G06F 19/327 705/2 |
| 2012/0203785 A1 | 8/2012 | Awada | |
| 2013/0314210 A1 | 11/2013 | Schoner | |
| 2014/0035726 A1 | 2/2014 | Schoner | |
| 2015/0213225 A1 | 7/2015 | Amarasingham | |

* cited by examiner

COMPUTER-IMPLEMENTED SYSTEM AND METHOD FOR REAL-TIME FEEDBACK COLLECTION AND ANALYSIS

FIELD

This application relates in general to obtaining feedback and, in particular, to a computer-implemented system and method for real-time feedback collection and analysis.

BACKGROUND

Keeping customers happy is crucial to ensuring a business' success since happy customers return for further business dealings and provide referrals to potential customers. Hospitals are especially concerned with their patients' satisfaction since the federal government is focusing on providing financial incentives for hospitals to provide better care, including awarding hospitals with high patient satisfaction, while penalizing hospitals with lower levels of patient satisfaction. For example, under the Affordable Care Act of 2010, payments to hospitals that are beneficiaries of Medicare Advantage plans are based on patient satisfaction using a survey provided by the government. Hospitals with high scores will receive a bonus payment, while hospitals with low scores will lose money. Specifically, the Hospital Consumer Assessment of Healthcare Providers and Systems (HCAHPS) Survey is a standardized national survey with 32 questions for patients to provide information regarding their hospital experience, which allows comparisons to be made across hospitals using common factors. A portion of payment from the Centers for Medicare & Medicaid Services to hospitals subject to the Inpatient Prospective Payment System annual payment is linked to hospital performance, as determined by the HCAHP survey.

Currently, businesses, including hospitals, are able to determine and track customer satisfaction using surveys, either in hardcopy or electronic form. For instance, after a patron has finished dining at a restaurant, an electronic survey may be sent via email to ask the patron to grade multiple services provided by the restaurant, including the taste and quality of food, and customer service. In a further example, hospitals often mail a hardcopy survey to a patient a couple weeks after the patient has been discharged from the hospital.

However, asking a customer for feedback after that customer has already left the business establishment does not allow the business to correct any mistakes or satisfy the customer's concerns during the current visit, which can result in a loss of further patronage by that customer. After the service has been provided and feedback received, a business can try and entice a customer to return by offering discounts or free offers. Yet, sometimes a customer is so dissatisfied that the customer will not return despite the discounts and free offers. In contrast, providing a business with feedback during a customer's visit allows that business to rectify any concerns or dissatisfaction of the customer in a timely manner, which can result in repeat visits by that customer.

Therefore, there is a need for obtaining customer feedback during the customer's visit and determining a satisfaction level of the customer based on the feedback. Preferably, any dissatisfaction of the customer can be resolved during the current visit to encourage further patronage.

SUMMARY

Receiving feedback from patients in real-time allows a hospital to correct any errors made during the current patient visit and increase patient satisfaction so that the patient does not leave the hospital with unfavorable impressions about the care provided or the hospital stay. A patient can provide feedback on his/her own initiative or in response to prompts provided via, for example, a watch, telephone call, text message, software application on a computer, TV display or smartphone, or other hospital equipment. The prompt can be transmitted to the patient after an interaction between the patient and another individual, such as a hospital employee, is detected. Prompts can also be triggered by a patient location, a defined time, or after a specific procedure is performed on the patient. Subsequently, the feedback is analyzed to determine a level of the patient's satisfaction with respect to one or more entities, including the individual with whom the patient interacted with and the hospital in which the interaction took place. Based on the satisfaction level, appropriate action can be taken with the intention of increasing the patient's satisfaction. Additionally, the satisfaction levels of the patient can be combined with other patient's satisfaction levels for a particular entity to generate a satisfaction score. The scores for two or more entities can be compared to determine which entity is providing better service and receiving higher patient satisfaction.

An embodiment provides a computer-implemented system and method for real-time feedback collection and analysis. An event related to a patient is identified during the patient's visit to a medical care facility. A prompt soliciting feedback is triggered upon identification of the event and the prompt is provided to the patient with at least one inquiry regarding the event. Feedback regarding the event is provided by the patient during the patient's visit to the medical care facility in response to the prompt. The feedback is analyzed and a recommendation for intervention of the patient's care is provided during the patient's visit to the medical care facility based on the feedback analysis.

A further embodiment provides a computer-implemented method for real-time feedback collection and analysis. A visit of a patient at a medical care facility is monitored. Feedback regarding satisfaction of care provided by the medical care facility is received from the patient during the patient's visit. The feedback is analyzed and a recommendation for intervention of the patient's care is provided during the patient's visit to the medical care facility based on the feedback analysis.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Since the Affordable Care Act was enacted in 2010, many hospitals are focusing on increasing the quality of care provided and patient satisfaction since money distributed by Medicare is driven by hospital scores for performance. For example, the Centers for Medicare & Medicaid Services has set up specific surveys, which are used to determined value based incentive payments to qualifying hospitals depending on performance by the hospital. Currently, hospitals send surveys to patients after they have already completed their stay and the feedback received can be used to improve quality and satisfaction scores of the next patients. However, the hospitals are unable to improve or remove any negative scores from the current patient surveyed, which may negatively affect the overall scores and eventually result in a loss of benefits for the hospital. Receipt of patient scores and feedback in real-time allows hospitals to immediately improve care of the patient during the current stay and the patients are more likely to leave the hospital with a favorable opinion about their experience.

Figure 1:
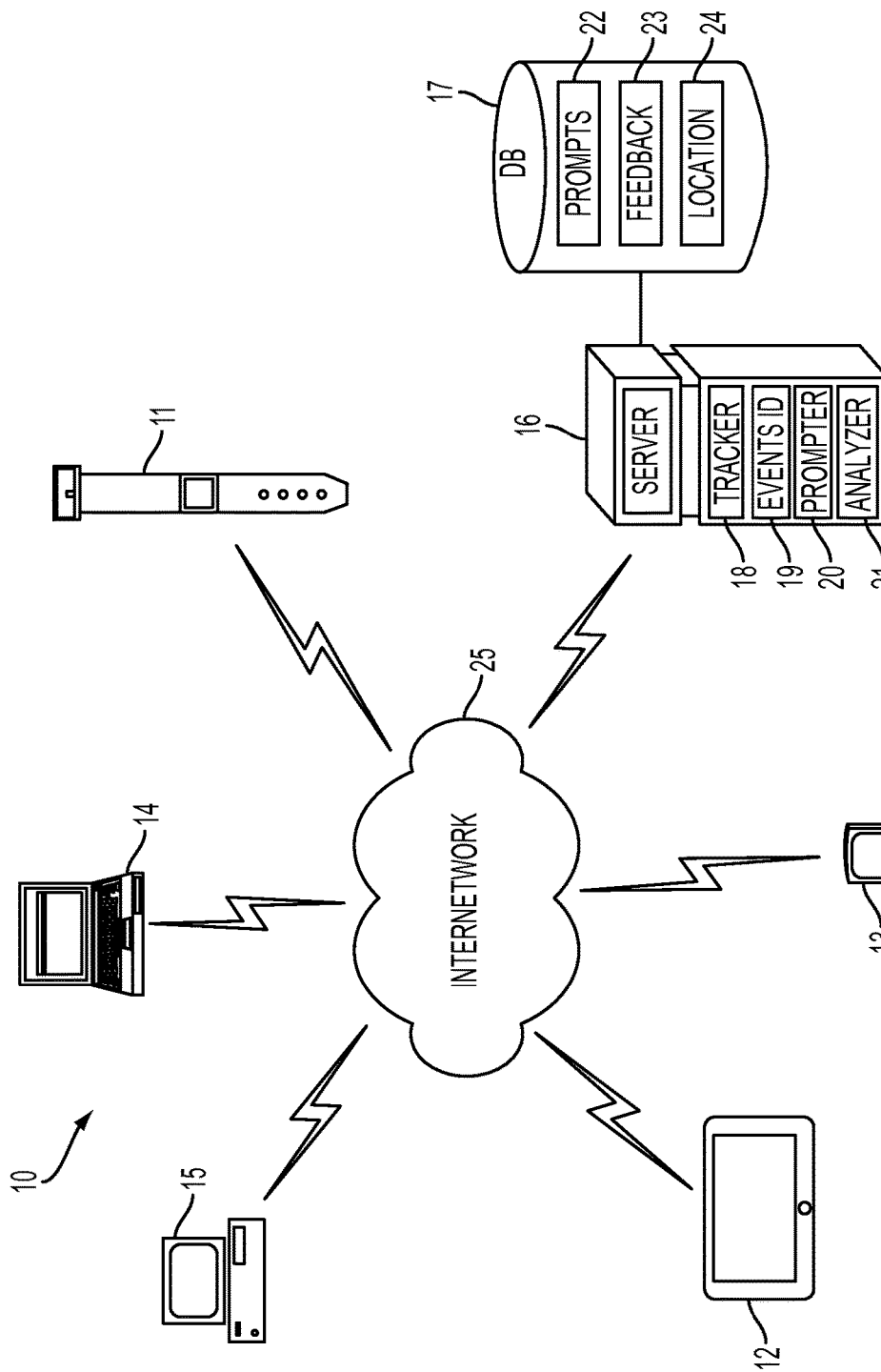
FIG. 1 is a block diagram showing a computer-implemented system for real-time feedback collection and analysis, in accordance with one embodiment.

Obtaining feedback during a patient's stay requires a device for collecting the patient feedback. FIG. 1 is a block diagram showing a computer-implemented system 10 for real-time feedback collection and analysis, in accordance with one embodiment. A patient admitted to a hospital can be associated with a device, such as a watch 11, cellular telephone 13, tablet 12, laptop 14, desktop computer 15, television (not shown), or other device that can receive feedback from a patient. Each of the watch, cellular telephone, tablet, and laptop can be interconnected to a server 16 via an internetwork 25, including the Internet. The server 16 includes a tracker 18, an events identifier 19, a prompter 20, and an analyzer 21. The tracker 18 can determine a real-time location 24 of the patient from which feedback is solicited, as well as hospital employees, as further described below with reference to FIG. 4. Subsequently, the events identifier can use the location of the patient and one or more employees to determine an event, such as an interaction between the patient and one of the employees, about which patient feedback can be obtained. Determining events is further discussed below with reference to FIG. 3. Upon identification of an event, the prompter 20 can transmit a prompt 22 for feedback to the device associated with the user. The prompt 22 can be stored in a database 17 interconnected to the server 16. Feedback 23 received from the user is then transmitted to the server 16, processed by the analyzer 21, and stored in the database 17.

The devices 11-14 and feedback server 16 each include components conventionally found in general purpose programmable computing devices, such as a central processing unit, memory, input/output ports, network interfaces, and non-volatile storage, although other components are possible. Moreover, other information sources in lieu of or in addition to the servers, and other information consumers, in lieu of or in addition to the handsets and computers, are possible.

Additionally, the devices 11-14 and server 16 can each include one or more modules for carrying out the embodiments disclosed herein. The modules can be implemented as a computer program or procedure written as source code in a conventional programming language and is presented for execution by the central processing unit as object or byte code or written as interpreted source code in a conventional interpreted programming language interpreted by a language interpreter itself executed by the central processing unit as object, byte, or interpreted code. Alternatively, the modules could also be implemented in hardware, either as integrated circuitry or burned into read-only memory components. The various implementations of the source code and object and byte codes can be held on a computer-readable storage medium, such as a floppy disk, magnetic or solid-state hard drive, digital video disk (DVD), random access memory (RAM), read-only memory (ROM) and similar storage mediums. Other types of modules and module functions are possible, as well as other physical hardware components.

Figure 2:
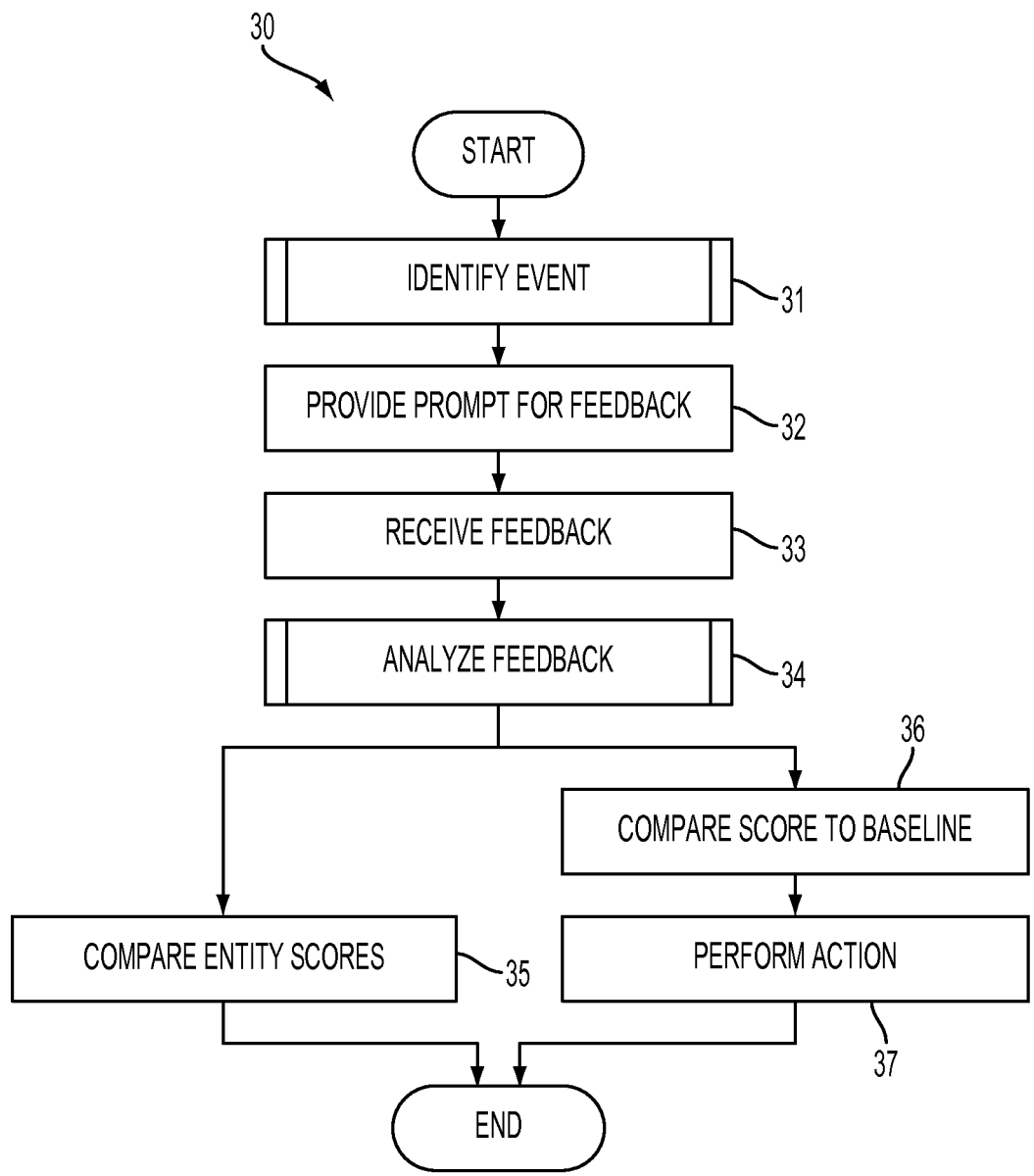
FIG. 2 is a flow diagram showing a computer-implemented method for real-time feedback collection and analysis, in accordance with one embodiment.

Real-time feedback can be patient initiated or provided in response to a prompt. FIG. 2 is a flow diagram showing a computer-implemented method 30 for real-time feedback collection and analysis, in accordance with one embodiment. Upon admittance to a hospital, a patient can be associated with a device that can collect feedback data. The device can include a watch, cell phone, tablet, or a particular piece of hospital equipment, such as a bed with a receiver and transmitter, or a remote control that can receive feedback for analysis. The patient can be monitored to determine (step 31) an event that may result in useful feedback. The event can include an encounter with a hospital employee, a defined time, a location of the patient, or a procedure performed upon the patient. Upon detection of the event, a prompt for soliciting feedback can be transmitted (step 32) to the patient's device. The prompt can include one or more questions asking the patient to rate his/her experience and provide his/her satisfaction level regarding the event. Specifically, the questions can focus on the patient's condition or an entity associated with the patient, including a hospital employee or the hospital itself. In response to the prompts, the patient can provide feedback (step 33) via the device. The prompts can be helpful in obtaining truthful feedback from a patient who may otherwise be embarrassed or unwilling to provide the feedback to a person, such as a nurse. The feedback can include satisfaction scores based on numerical values, binary values, such as yes or no answers, and short phases or sentences. The feedback is then analyzed (step 34) to determine a score for one or more patient conditions or entities. Analyzing the feedback is further defined below with reference to FIG. 6.

The score can be used to determine whether any action should be performed (step 37) to increase the patient's satisfaction levels, change hospital procedure, or award or discipline employees. Specifically, the scores can be compared to a patient baseline (step 36), which is a measurement of initial feedback scores provided by the patient. The baseline can be determined as an average or median value of the initial feedback scores, or as a moving average as further described below. As an example, a baseline can be generated for a patient's pain level. The patient generally indicates pain level at a 3 or 4 and has a baseline of 3.5, with the highest pain indicated by a score of 10. However, if the patient provides feedback that his/her pain level is at a 6, action may occur since the patient's feedback indicates that his/her pain level is at a much higher level than normal. The action can include intervention with respect to the patient's care, such as administration of stronger pain medication, as well as a review of the patient's pain management plan, and can occur based on a recommendation from the system or based on the comparison of the score and the baseline. In contrast, an action is unlikely to occur for a patient that provides his/her pain level at a 6, when his/her baseline pain level is around a 5. Baselines can also be used for other patient conditions, such as satisfaction, depression, tiredness, or loneliness, as well as other situations that may impact patient satisfaction.

Additionally, a baseline can be generated for groups of patients across different medical care facilities or different units of the same facility. For example, patients that are admitted to the orthopedic ward of the hospital generally experience more pain than those patients in the maternity ward who have already delivered their babies. Thus, the baseline for the patients in the orthopedic ward is likely higher than the patients in the maternity ward, where pain generally occurs during labor and delivery, but not usually after. A patient that indicates high pain after delivering her baby, may have a medical emergency or other complication that should be addressed by a nurse or doctor.

In a further embodiment, an employee baseline can be used to determine whether an employee needs additional training or reprimanding. An employee that consistently receives negative feedback relative to peers in the same or comparable position or level of responsibility should be reviewed to determine why the scores provided by the patients are consistently low. The comparison can occur among employees in the same or comparable positions to account for the different types of practices and patient conditions within those practices. For instance, oncology nurses may deal with patients that experience chronic pain who tend to provide lower performance scores, than nurses in a maternity ward with many patients that are ecstatic about delivering a baby. Further, a comparison of scores from patients based on overall patient prognosis can be made. Alternatively, an employee that has a high baseline for patient satisfaction, but recently receives low scores, may be dealing with a personal problem that is affecting her job or may be unhappy with her job, and such a situation may need to be investigated in a timely fashion before patient care is impacted.

With respect to hospitals, branches, or departments within a hospital, an entity baseline can be used to determine whether the hospital needs to take action to improve medical services or hospital conditions. The entity baseline can be determined as an average or median value of scores provided to the hospital in the same or comparable categories of feedback or of all feedback scores received.

The feedback score for an entity can also be compared (step 35) with scores for other entities to analyze performance. For example, a nurse may receive high satisfaction feedback scores, but in relation to other nurses on her floor, she may have the lowest scores of all the nurses. Information obtained from the nurses with the higher scores can be used for training purposes. In a further example, a hospital can have multiple branches located in different cities. The scores associated with the hospital for one or more categories, including care, cost and performance of specific departments, can be compared with the other branches to determine which branches or departments are performing well and which ones need improvement. Procedures and best practices followed in the highest scoring branch or department can be implemented in the other branches or departments in an attempt to increase the scores of the other branches and departments.

Figure 3:
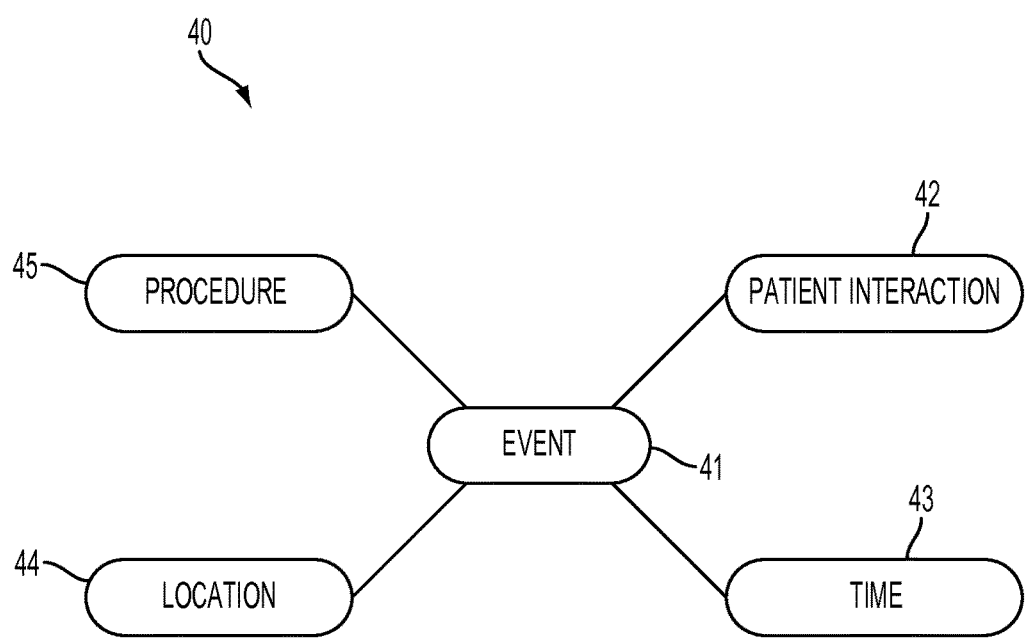
FIG. 3 is a block diagram showing, by way of example, methods for detecting an event that prompts feedback collection.

The determination of one or more events can be used to trigger a prompt for feedback. FIG. 3 is a block diagram showing, by way of example, methods 40 for detecting an event 41 that prompts feedback collection. The events 41 can include an interaction 42 event, a defined time 43 event, a location 44 event, and a procedure 45 event, as well as other types of events after which patient feedback can be solicited and collected. An interaction 42 event can include an interaction between a patient and another individual, such as a hospital employee or representative of the hospital. Triggering a prompt immediately after a patient interaction encourages feedback about that interaction while the interaction is fresh in the patient's mind and also provides an opportunity to take corrective action that may change any negative impressions the patient may have as a result of the interaction.

Figure 4:
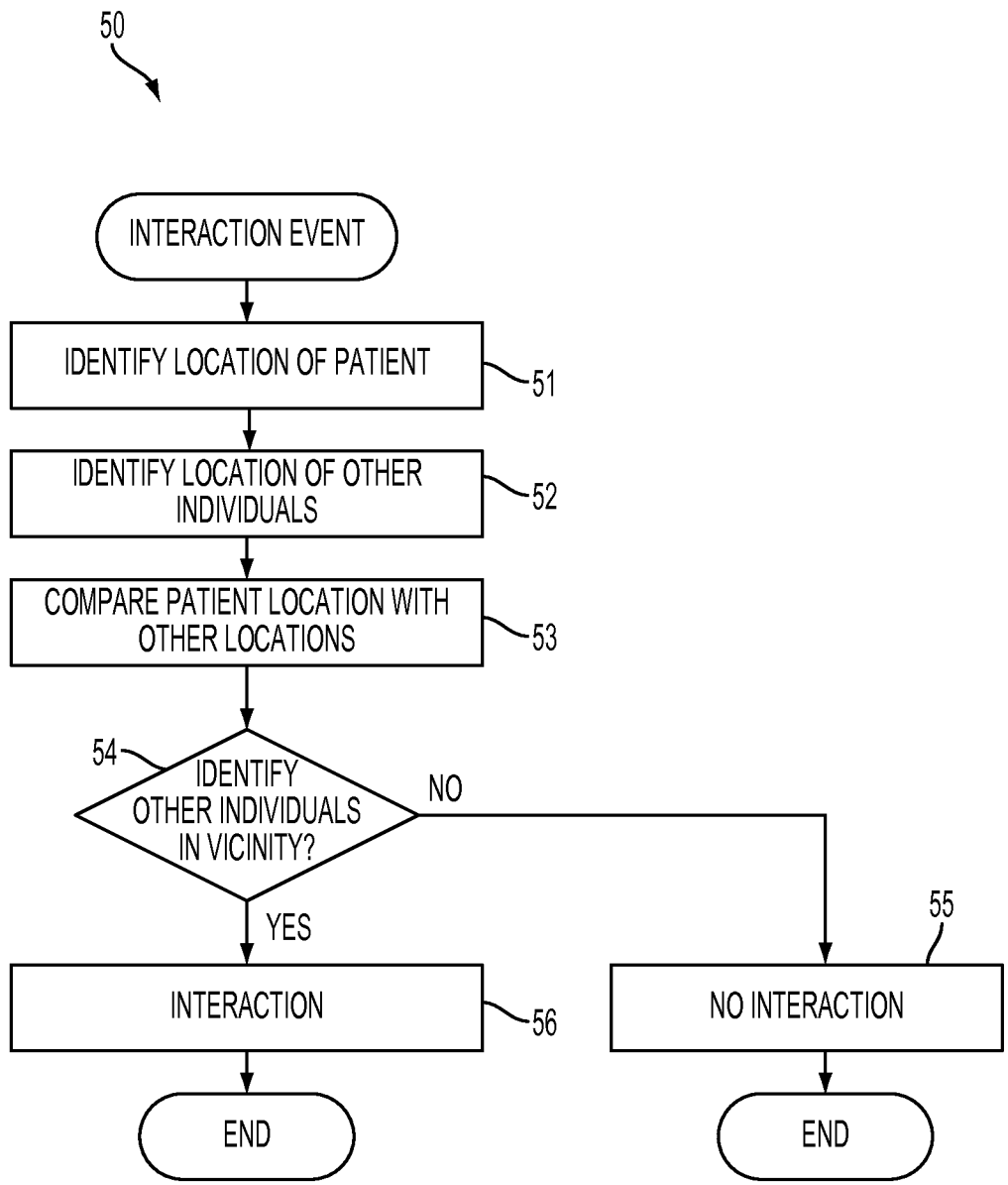
FIG. 4 is a flow diagram showing, by way of example, a process for determining an interaction event.

An interaction 42 between a patient and another individual can be identified by tracking a location of individuals within a hospital, as described in further detail in commonly-owned U.S. patent application, Publication No. 2015/0310180, filed on Apr. 25, 2014, and in commonly-owned U.S. patent Application Publication No. 2015/0309156, filed on Apr. 25, 2014, the disclosures of which are hereby incorporated by reference. The locations and location histories of the individuals can be compared to determine whether two or more of the individuals are participating in a conversation. FIG. 4 is a flow diagram showing, by way of example, a process 50 for determining an interaction event. Each individual within a hospital can be associated with a tracker, such as an RFID tag. The RFID tag can be embedded in a patient identification bracelet, as well as an employee identification card used to clock in and out of the hospital and access restricted areas. A location of the patient is identified (step 51) by tracking the RFID tag associated with the patient using RFID readers positioned strategically throughout the hospital. The locations of other individuals in the hospital are also determined (step 52) by tracking the RFID tags associated with those individuals. The location of the patient is compared (step 53) with the locations of the other individuals and a determination (step 54) is made as to whether any individual is within a predetermined vicinity of the patient's location. If none of the other individual's locations are determined to fall within the predetermined vicinity, no interaction between the patient and the other individuals is identified (step 55). If the location of one or more of the other individuals is determined to be within the vicinity of the patient location, an interaction between the patient and that other individual is identified (step 56). The identified interaction event (step 56) is then used as a trigger for transmitting a prompt soliciting feedback from the patient, as appropriate.

In a further embodiment, an interaction 42 between the patient and another individual can be determined by reviewing the patient's electronic record or the doctor's daily schedule of patient appointments. Thus, a prompt can be triggered upon identification of the patient's appointment with the doctor, upon entry of the doctor's notes in the patient's electronic record, or upon entering of the patient's vital signs by a caregiver into an electronic medical record for that patient.

A defined time 43 event can include scheduling the prompts, such as on a periodic or regular basis. The time prompts can be used to monitor pain, track breast feeding, ensure patient comfort, and maintain overall patient satisfaction. For example, a regular prompt can be sent to a patient with high pain levels to monitor how much pain the patient is experiencing over time and whether the current pain treatment is effective. If the patient indicates he/she is in pain, a nurse can review the patient's pain management and make any adjustments, if necessary, including administering additional pain medicine. Patients in pain may be less satisfied or have a more negative feeling regarding their care than those patients who experience less pain. Appropriate normalization of the feedback data to account for such situations can therefore be carried out to interpret the feedback in terms of the patient's situation. In a further example, a prompt can be provided during or after a patient has eaten a meal prepared by the hospital. The prompt can include a general question, such as "did you enjoy the food during your stay?" or specific questions, including, inter alia, "how was the baked chicken and carrots?" or "please rate your lunch of baked chicken and carrots." The feedback received from the patient can be used to remove any dishes disliked by the patient and add new dishes. In yet a further example, a general "how are you feeling" prompt can be sent to periodically monitor patient wellbeing and mental health.

A location 44 of the patient can be monitored and used to trigger a prompt, thereby allowing the hospital to receive unique feedback that may not be received using conventional surveys provided after the patient's release. For example, a prompt can be provided during or immediately after the patient is determined to be within a restroom or a common area of the hospital, such as a waiting room. If most patients rate a particular room or waiting area as unlikeable, the hospital may need to upgrade the room. Additionally, if the feedback indicates that a particular restroom is always dirty, the assigned janitor may not be doing a good enough job of cleaning the restroom and the hospital can take steps to ensure that the janitor does a better job of cleaning the restroom.

Medical procedures 45 can be used as events to allow the patient to rate the procedure immediately or soon after performance of that procedure. In contrast with conventional surveys that are provided after the patient has completed his/her stay at the hospital, receiving feedback during the patient's stay can help the hospital to fix or change any negative views by the patient. For example, a patient is unhappy with a knee replacement surgery that has just been performed because the patient believes the incision is too large. Based on this feedback, the doctor can talk with the patient about the incision and explain why the incision size was necessary. If the patient understands the reason for the incision size, he/she may have more positive feelings about the surgery than if the patient continued to believe the incision is unnecessarily large.

One or more of the triggering events may occur simultaneously or near-simultaneously, such as a doctor performing a surgery upon the patient, which would trigger a patient interaction event and a procedure event. In one embodiment, a single prompt can be transmitted to the patient with questions directed to both the doctor's performance and the surgery itself. Alternatively, separate prompts can be sent. In yet a further embodiment, a record of the triggers is maintained to determine when the triggers occurred. The trigger record can then be used to prevent solicitation for feedback at inconvenient times, such as during the night.

The prompts can be received throughout the patient's hospital stay. In one example, a patient is in labor and travels to the hospital. Upon entry, the patient is taken to triage, where the patient's condition is assessed by a nurse. While in triage, the patient is provided with a feedback device, either by the nurse or another employee. A prompt can be transmitted to the feedback device requesting feedback regarding the patient's condition and pain levels upon entry to the hospital, as well as the interaction between the patient and the nurse.

When the patient is determined to be in labor, the patient is admitted to the hospital and moved to a birthing room, where the patient may be given an epidural to ease the pain of contractions. A further prompt for feedback can be transmitted to the user device based on the patient's location within a new room and the optional administration of an epidural. Throughout the patient's labor, prompts can be sent to ensure that the patient is in good spirits and her pain is adequately managed. Additionally, a prompt can be delivered to the device after delivery of the patient's baby and throughout the remaining stay of the patient to ensure the patient's stay is comfortable and all her questions are answered.

Figure 5:
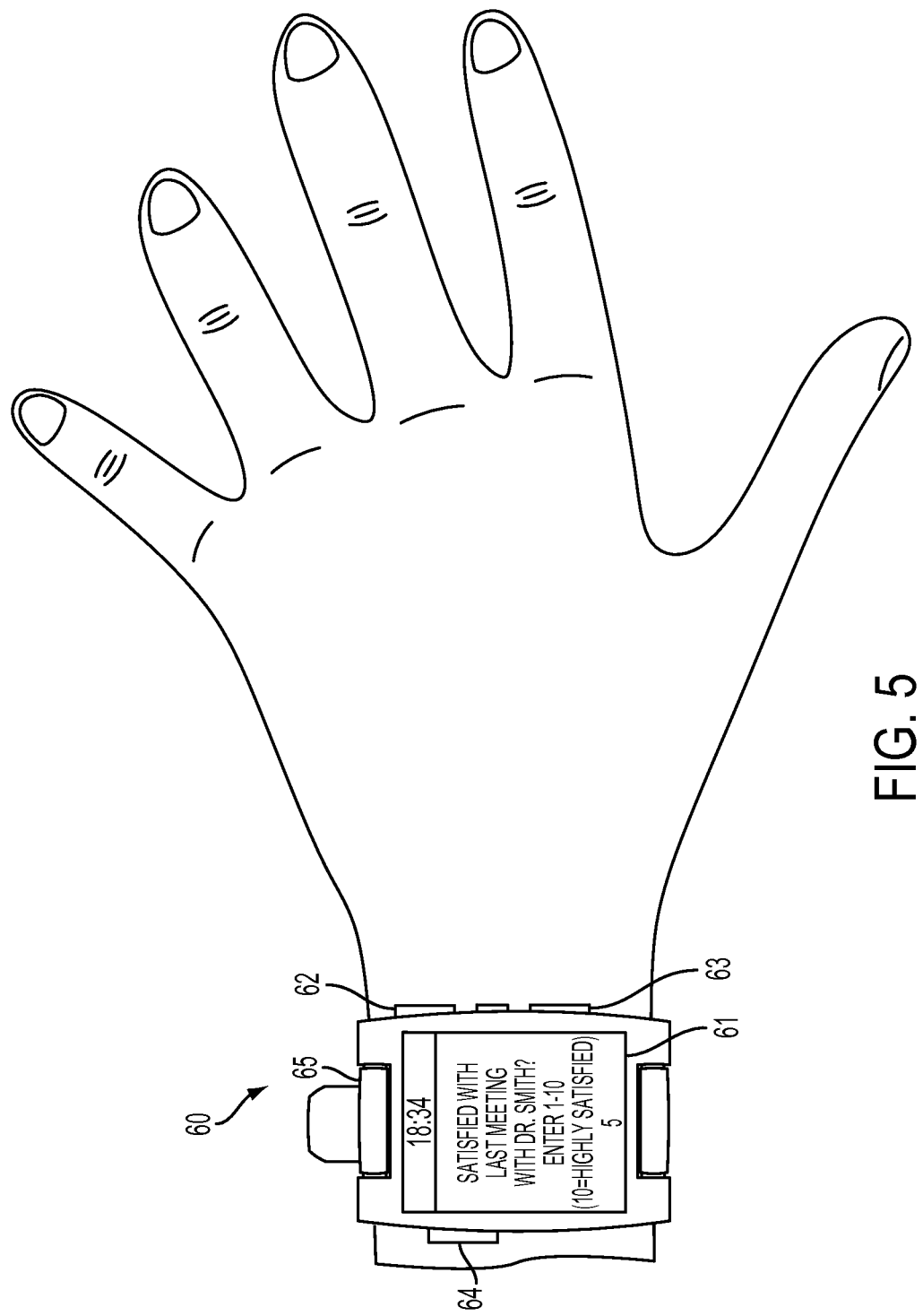
FIG. 5 is a block diagram showing, by way of example, a wrist band for collecting real-time feedback.

Upon receipt of the prompts, the patient can provide feedback in response. The feedback can be collected from the patient via a watch worn by the patient or a cellular telephone. FIG. 5 is a block diagram showing, by way of example, a watch for collecting real-time feedback. The watch can be provided to the patient upon being admitted to the hospital and can be reusable or disposable. The watch 60 can include a strap 65 and a watch face 61 on which a prompt can be displayed. In one embodiment, a strap of the wristband can include identification information of the patient.

The patient can wear the watch on his/her wrist, and once an event has been detected, a prompt is triggered and displayed on the watch face 61. The prompt can include one or more questions to which feedback from the patient is requested. The questions can be based on the type of event detected. For example, if an interaction event is detected, the questions can focus on an individual with whom the patient is interacting, including impressions about the interaction, the patient's satisfaction with the individual's performance during the interaction, and characteristics of the individual, such as whether the individual was professional, friendly, or knowledgeable. Questions regarding a time event can focus on a particular malady, reason, such as monitoring pain or nursing, or general wellbeing of the patient. Specific questions can include "what is your pain level?" "how is nursing going?" or "how are you feeling?" Other types of questions are possible. A location event can trigger questions regarding the location in which the patient is positioned, including, inter alia, common areas of the hospital, the patient's room, and restrooms. The questions can focus on a décor, cleanliness, population of individuals, noise level, and aesthetics of the location, as well as other aspects. Meanwhile, questions focusing on a procedure event can focus on pain experienced during with the procedure, whether sufficient staff was present to assist in the procedure, whether the patient's requests were followed, and recovery. The questions can include "how was your knee surgery," "how much pain did you experience during the surgery," and "did the staff follow up on any requests made?" The questions soliciting feedback can be provided to the patient randomly, in a predetermined order, or in a hierarchical manner, such that a question to be provided to the patient is determined based on previous feedback from the patient in response to a question asked.

In one embodiment, the patient can provide feedback in response to the asked questions via the watch 60. Specifically, the feedback can be provided by entering a numerical value within a predetermined range for each question displayed. The desired number can be entered using a "plus" button 62 or a "minus" button 63. For instance, a first question can be displayed with directions to enter a number from one to ten with ten representing high satisfaction. A number can be displayed and the patient can increase or decrease the number using the "plus" 62 or "minus" 63 buttons, respectively. In one example, a five can be initially displayed since five is midway between one and ten. However, other numbers can be initially displayed. Alternatively, the questions displayed can elicit a yes or no response. To provide a "yes" reply, the patient can hit one button 62, while a different button 63 can be selected for a "no" reply. In a further embodiment, the watch can include a keypad or a digital keypad that can be displayed within the face of a smart watch for the patient to enter feedback, including numerical values or text.

In a further embodiment, a wristband can be provided with two moveable fasteners that each surround the band. Color coded cards or numbered cards can placed on the wristband and secured with the fasteners on top and bottom sides of the cards. The color coded card and numbered cards are placed on the band as a reply of feedback to a particular question. As described above, the numbers can provide a level of satisfaction, while the colors can each represent a different level of satisfaction that can later be quantified. A camera located within the patient's hospital room can photograph the card placed on the patient's wristband and image analysis can be performed to determine the feedback from the patient.

In lieu of a watch, feedback can also be provided by the patient via existing medical equipment that is customarily located within a patient's room, such as a hospital bed, remote control, or nurse call button. For example, a speaker or display can be built into the nurse call button, along with a receiver for receiving the prompts for display, and a transmitter for sending feedback received from the patient to a server for analysis.

Additionally, the patient can provide feedback via a smart phone using a computer application or "app," text messaging, Instant Messing, email, or voice calls. The feedback can be provided as text data, voice data, numerical values, or binary values, such as "yes" or "no" replies. The prompts can also be transmitted to and displayed via the smart phone. When an app is used, the patient can register and login to the app upon arrival at the hospital and the prompts are then sent to the patient via the app. Upon receipt of the prompt, the smart phone can provide notice of the prompt to the patient by a sound or vibration. If the patient desires to provide feedback via text messaging, Instant Messaging, email or voice calls, the patient must provide his/her telephone number, screen name, or email address so that the prompts can be transmitted to the patient's phone or email account.

When feedback is provided as text, the text can be analyzed using natural language processing to determine a meaning or sentiment of the text. Further, voice utterances received from the patient as feedback, such as via a telephone call, can be analyzed to determine the patient's responses, as well as provide additional information regarding the feedback data based on a volume, pitch, pauses, intonation, breathiness, nasality, speed, and resonance frequencies of the patient's speech. Additionally, when the prompts are provided via spoken dialogue, such as via a telephone call or through a speaker located in a piece of medical equipment or watch, the spoken dialogue can include synthesized speech. The synthesized speech can be prerecorded scripts or generated and played to the patient using a text-to-speech engine.

Figure 6:
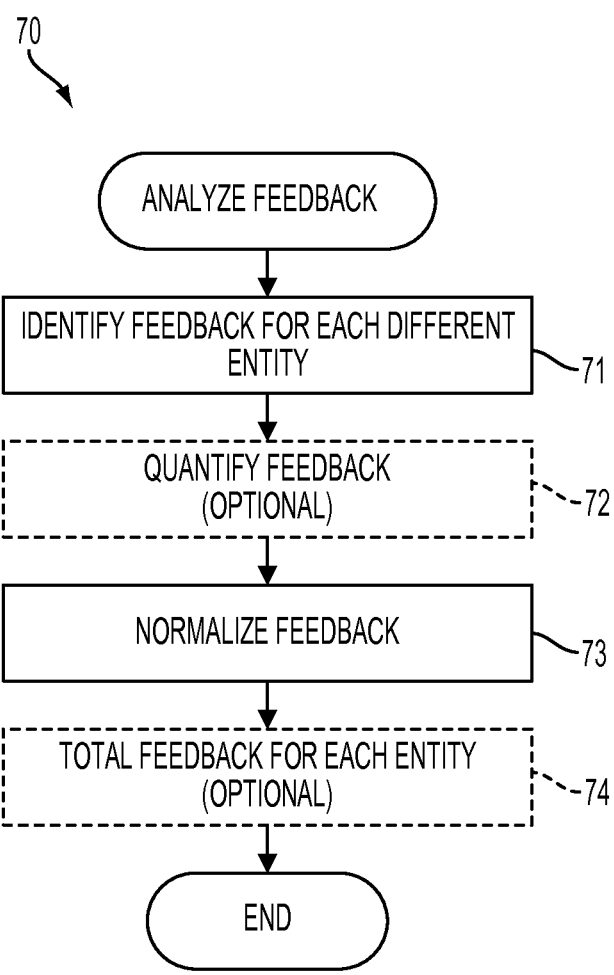
FIG. 6 is a flow diagram showing, by way of example a process for analyzing feedback.

The feedback can be analyzed to obtain a quantitative score. FIG. 6 is a flow diagram showing, by way of example a process for analyzing feedback. As described above, each prompt can include multiple questions for which feedback is received. Responses to the questions are assigned (step 71) to the entity to which the question refers. For example, feedback received in response to the question "are you satisfied with the last meeting with Dr. Smith" is assigned to Dr. Smith. If the received feedback is not provided as a quantitative value, the feedback is processed (step 72) to assign a quantitative score. When colors are used as feedback, each color can represent a patient's satisfaction level in response to a given question that can be translated to a numerical value. Further, when "yes" and "no" response are provided as feedback, each response can be associated with a different quantitative value that represents the patient's satisfaction or lack of satisfaction with respect to the entity in question.

The feedback scores can be normalized (step 73) to account for scoring differences between patients using a baseline for one or more of the patients. Scores from patients who generally score below the average or from patients that generally score above the average can be adjusted. In one example, a patient gives Dr. Smith a score of 7 for performance, with 10 representing the most satisfied, while the average score associated with Dr. Smith's performance is a 9. However, upon review of the patient's scoring history, this patient is determined to generally provide feedback with low scores in the range of around 5 or 6. The patient's scoring history can be based on a predetermined number of initial scores received as feedback, starting when the patient is first admitted to the hospital. Then, based on the patient's history, if the score of 7 provided by the patient is much higher than normal, the score is adjusted to reflect the higher than average satisfaction of the patient. The adjusted score is then added to the existing average score for Dr. Smith. Further, quantitative values from different types of feedback can be normalized before being added to the average score. Any scores that are too far removed, either higher or lower, from the average score can be deleted or reviewed for accuracy and relevance.

In a further embodiment, a moving average of ongoing last n scores can be used to reevaluate normalization of the feedback using a patient baseline from time to time and to compare average patients. For example, when n equals 10, the ten most recent scores from the patient are used to generate the baseline. As the patient provides more scores the ten most recent scores used to determine the baseline change to reflect the ongoing feedback provided by the patient. A moving average baseline can help to normalize the scores of a patient who has extreme experiences during the hospital stay. A woman who is in labor and admitted to the hospital is generally in a lot of pain and may provide lower satisfaction scores due to the natural pain experienced. However, when the patient receives an epidural, some of the pain should subside and the patient may provide higher scores based on an easing of the previous pain. Finally, after the patient's baby is placed in her arms, the patient is likely to provide even higher scores due to the joy and excitement at seeing her new baby.

Subsequently, the feedback can optionally be added (step 74) to an existing score for the patient or to an existing score for previous feedback from other patients for the same entity, for instance, Dr. Smith. The existing score can be determined as a cumulative score of all the feedback or as an average of the feedback received.

In a further embodiment, each entity can be associated with scores for different categories. For a hospital employee, the categories can include, inter alia, performance, personality, and bedside manner. Categories for a hospital can include overall performance, privacy, amenities, food, condition, cost, accommodations, and security. Other types of categories for the entities are possible. When multiple categories exist for an entity, a category for a specific quantitative value is determined, such as based on the type of question asked. Subsequently, the quantitative value is added to the cumulative or average score for the existing feedback from previous patients.

In addition to or in lieu of providing feedback in reply to a prompt, a patient can also provide feedback at any desired time. As described above, the feedback received from the patient can include text data, numerical values, and binary values. The text can be processed using natural language processing to determine meaning or sentiment of the text. An entity to which the feedback applied can also be determined. Based on the determined meaning or sentiment for the identified entity, a quantitative value can be assigned. If only a numerical value or binary value is received, the hospital can be identified as a default entity, in one embodiment, and the received value can represent the patient's general satisfaction regarding his/her stay.

Upon the patient's discharge from the hospital, a survey can be mailed or otherwise transmitted to the patient via email or text message. The feedback received during the patient's stay can be used to guide the questions provided in the survey to determine whether any concerns of the patient remain.

The feedback provided by the patient can also be provided to a designated person who assists in managing the patient's care, such as a family member, friend, or outside caregiver. In one example, when the patient is admitted to the hospital, the designated individual provides contact information, such as a telephone number or email address at which the designated individual can receive the patient's feedback.

In a further embodiment, patient feedback can also be obtained from the patient's designated individual since a patient may not always be willing to or may be embarrassed to disclose a particular patient condition. Asking the patient's designated individual for feedback may help the patient receive the care needed, even if he/she is unwilling to ask for the care.

Although collecting feedback and analyzing the feedback has been described with respect to a patient's stay in a hospital, the feedback collection and analysis can also occur during or after a patient's visit to any type of medical care facility, such as an outpatient doctor's office, nursing home, or rehabilitation center. Other types of medical care facilities are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A computer-implemented system for real-time feedback collection and analysis, comprising:
    a patient device to collect data regarding a patient during a visit to a medical care facility;
    a server comprising memory, a central processing unit, an input port to receive the data from the patient device, and an output port, wherein the central processing unit is configured to:
        identify an event comprising an interaction between the patient and another individual, comprising:
            determine a location of an RFID tag associated with the patient and a location of another RFID tag associated with the other individual based on known coordinates of RFID readers that identify the RFID tags;
            compare the location of the RFID tag associated with the patient with the location of the other RFID tag associated with the other individual;
            apply a predetermined threshold to a distance between the RFID tag and the other RFID tag; and
            determine the interaction event when the RFID tag is within the predetermined threshold of the other RFID tag;
        automatically transmit a prompt soliciting feedback upon identification of the event and generate inquiries through the prompt based on the identified event;
        analyze feedback from the patient regarding the event during the patient's visit to the medical care facility in response to the prompt; and
        automatically provide a recommendation during the patient's visit for intervention in delivery of care to the patient based on the feedback analysis; and
    a third party device to receive the recommendation for intervention in care of the patient during the patient's stay, wherein the intervention identified by the patient feedback is performed during the patient's stay.

2. A system according to claim 1, further comprising:
    a feedback module to receive patient-initiated feedback and to analyze the patient-initiated feedback with the feedback received in response to the prompt.

3. A system according to claim 1, further comprising:
    a recipient identification module to identify one or more entities as recipients of the feedback, wherein the entities comprise at least one of the medical care facility, departments within the medical care facility, branches of the medical care facility, individual employees of the medical care facility, and groups of employees at the medical care facilities.

4. A system according to claim 3, further comprising:
    a feedback collection module to collect feedback from other patients associated with the entity;
    a scoring module to generate an average score of patient satisfaction for that entity based on the feedback from the patient and the other patients; and
    a comparison module to compare the score for the entity with scores for other entities.

5. A system according to claim 1, further comprising:
    a transmission module to transmit prompts to the patient at predefined times inquiring about the patient.

6. A system according to claim 1, wherein the feedback is collected from the patient via a watch, smart phone application, hospital equipment, nurse call button, telephone, verbal utterances, text message, and email.

7. A system according to claim 1, wherein the analysis module further comprises:
    a score module to generate a score for the feedback received from the patient;
    a baseline module to generate a baseline for the patient, comprising at least one of:
        an initial baseline for the patient based on a predetermined amount of initial feedback provided by the patient; and
        a moving average baseline of n most recent items of the feedback provided by the patient;
    comparing the score with the baseline; and
    determining the recommendation for intervention.

8. A computer-implemented method for real-time feedback collection and analysis, comprising:
    collecting data regarding a patient during a visit to a medical care facility via a patient device;
    identifying an event comprising an interaction between the patient and another individual via a server, wherein the server comprises memory, a central processing unit, an input port to receive the data from the patient device, and an output port, comprising:
   determining a location of an RFID tag associated with the patient and a location of another RFID tag associated with the other individual based on known coordinates of RFID readers that identify the RFID tags;
   comparing the location of the RFID tag associated with the patient with the location of the RFID tag associated with the other individual;
   applying a predetermined threshold to a distance between the RFID tag and the other RFID tag; and
   determining the interaction event when the RFID tag is within the predetermined threshold of the other RFID tag;
automatically transmitting via the server a prompt soliciting feedback upon identification of the event and generating inquiries through the prompt based on the identified event;
analyze from the patient, feedback regarding the event during the patient's visit to the medical care facility in response to the prompt;
automatically providing a recommendation for intervention in delivery of care to the patient based on the feedback analysis by the server; and
sending to a third party device the recommendation for intervention in care of the patient during the patient's stay, wherein the intervention identified based on the patient feedback is performed during the patient's stay at the medical care facility.

9. A method according to claim 8, further comprising:
receiving patient-initiated feedback; and
analyzing the patient-initiated feedback with the feedback received in response to the prompt.

10. A method according to claim 8, further comprising:
identifying one or more entities as recipients of the feedback, wherein the entities comprise at least one of the medical care facility, departments within the medical care facility, branches of the medical care facility, individual employees of the medical care facility, and groups of employees at the medical care facilities.

11. A method according to claim 10, further comprising:
collecting feedback from other patients associated with the entity;
generating an average score of patient satisfaction for that entity based on the feedback from the patient and the other patients; and
comparing the score for the entity with scores for other entities.

12. A method according to claim 8, further comprising:
transmitting prompts to the patient at predefined times inquiring about the patient.

13. A method according to claim 8, further comprising:
collecting the feedback from the patient via a watch, smart phone application, hospital equipment, nurse call button, telephone, verbal utterances, text message, and email.

14. A method according to claim 8, further comprising:
analyzing the feedback, comprising:
   generating a score for the feedback received from the patient;
   generating a baseline for the patient, comprising at least one of:
      calculating the baseline for the patient based on a predetermined amount of initial feedback provided by the patient; and
      calculating the baseline comprising a moving average of n most recent items of the feedback provided by the patient;
   comparing the score with the baseline; and
   determining the recommendation for intervention.

15. A computer-implemented method for real-time feedback collection and analysis, comprising:
monitoring a visit of a patient at a medical care facility and collecting data regarding the patient via a patient device;
determining an event comprising an interaction between the patient and another individual during which a medical procedure is performed by the individual on the patient, comprising:
   determining a location of an RFID tag associated with the patient and a location of another RFID tag associated with the other individual based on known coordinates of RFID readers that identify the RFID tags
   comparing the location of the RFID tag associated with the patient with the location of the RFID tag associated with the other individual;
   applying a predetermined threshold to a distance between the RFID tag and the other RFID tag; and
   determining the interaction event when the RFID tag is within the predetermined threshold of the other RFID tag; and
automatically sending a prompt to request data from the patient upon an occurrence of the event;
analyzing feedback provided by the patient in reply to the prompt via a server, wherein the server comprises memory, a central processing unit, an input port to receive the data from the patient device, and an output port;
automatically providing a recommendation for intervention in the delivery of care to the patient based on the feedback analysis by the server; and
sending to a third party device the recommendation for intervention in care of the patient during the patient's stay, wherein the intervention identified based on the patient feedback is performed during the patient's stay at the medical care facility.

16. A method according to claim 15, further comprising:
identifying one or more entities as recipients of the feedback, wherein the entities comprise at least one of the medical care facility, departments within the medical care facility, branches of the medical care facility, individual employees of the medical care facility, and groups of employees at the medical care facilities
collecting feedback from other patients associated with an entity;
generating an average score of patient satisfaction for that entity based on the feedback from the patient and the other patients; and
comparing the score for the entity with scores for other entities.

17. A method according to claim 15, further comprising:
collecting the feedback from the patient via a watch, smart phone application, hospital equipment, nurse call button, telephone, verbal utterances, text message, and email.

18. A method according to claim 15, further comprising at least one of:
analyzing the feedback, comprising:
   generating a score for the feedback received from the patient;

generating a baseline for the patient, comprising at least one of:
- calculating the baseline for the patient based on a predetermined amount of initial feedback provided by the patient; and
- calculating the baseline comprising a moving average of n most recent items of the feedback provided by the patient;

comparing the score with the baseline; and determining the recommendation for intervention.

19. A system according to claim 1, wherein the interaction comprises a medical procedure performed on the patient by the other individual.

20. A system according to claim 8, wherein the interaction comprises a medical procedure performed on the patient by the other individual.

* * * * *